(12) United States Patent
Sasaki (10) Patent No.: US 11,388,807 B2
(45) Date of Patent: Jul. 12, 2022

(54) X-RAY CT APPARATUS, X-RAY HIGH VOLTAGE APPARATUS, AND X-RAY CONTROL METHOD

(71) Applicant: CANON MEDICAL SYSTEMS CORPORATION, Otawara (JP)

(72) Inventor: Yu Sasaki, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/160,479

(22) Filed: Jan. 28, 2021

(65) Prior Publication Data
US 2021/0231590 A1 Jul. 29, 2021

(30) Foreign Application Priority Data

Jan. 29, 2020 (JP) .............................. JP2020-012336

(51) Int. Cl.
| H05G 1/08 | (2006.01) |
| H05G 1/34 | (2006.01) |
| H05G 1/26 | (2006.01) |
| A61B 6/03 | (2006.01) |
| A61B 6/00 | (2006.01) |

(52) U.S. Cl.
CPC ............ *H05G 1/085* (2013.01); *A61B 6/032* (2013.01); *A61B 6/54* (2013.01); *H05G 1/265* (2013.01); *H05G 1/34* (2013.01)

(58) Field of Classification Search
CPC .......... H05G 1/085; H05G 1/265; H05G 1/34; A61B 6/032; A61B 6/54
See application file for complete search history.

(56) References Cited

U.S. PATENT DOCUMENTS

| 4,481,654 A | * | 11/1984 | Daniels | ................ H05G 1/10 378/112 |
| 5,379,333 A | * | 1/1995 | Toth | ................ A61B 6/488 378/108 |
| 2003/0016778 A1 | | 1/2003 | Tachizaki et al. | |
| 2005/0018759 A1 | | 1/2005 | Underbrink et al. | |
| 2014/0161221 A1 | * | 6/2014 | Miyazaki | ............ H05G 1/085 378/16 |
| 2018/0228011 A1 | * | 8/2018 | Hirayama | ............ H05G 1/10 |

FOREIGN PATENT DOCUMENTS

| JP | 2005-230547 A | 9/2005 |
| JP | 4387638 B2 | 12/2009 |
| JP | 4746890 B2 | 8/2011 |

\* cited by examiner

*Primary Examiner* — Chih-Cheng Kao
(74) *Attorney, Agent, or Firm* — Oblon, McClelland, Maier & Neustadt, L.L.P.

(57) ABSTRACT

According to one embodiment, an X-ray CT apparatus includes processing circuitry. The processing circuitry is configured to acquire set tube current waveform, and specify, based on the set tube current waveform, a period of a first tube current and a period of a second tube current lower than the first tube current. The processing circuitry is further configured to determine a waveform of a grid voltage such that a first grid voltage is applied during a period corresponding to the period of the first tube current and a second grid voltage, which is higher than the first grid voltage, is applied during a period corresponding to the period of the second tube current.

7 Claims, 6 Drawing Sheets

X-RAY CT APPARATUS, X-RAY HIGH VOLTAGE APPARATUS, AND X-RAY CONTROL METHOD

CROSS-REFERENCE TO RELATED APPLICATIONS

This application claims the benefit of priority of Japanese Patent Application No. 2020-012336, filed Jan. 29, 2020, the entire contents of which are incorporated herein by reference.

FIELD

Embodiments described herein relate generally to an X-ray CT apparatus, an X-ray high voltage apparatus, and an X-ray control method.

BACKGROUND

Some X-ray CT (Computed Tomography) apparatus are capable of imaging with tube current modulation. In tube current modulation imaging, the tube current can be modulated according to the X-ray exposure angle with respect to the object and the position along the body axis of the object. Tube current modulation imaging allows the tube current to be modulated such that the thinner the specimen is, the smaller the tube current value becomes, thereby maintaining the image quality of the X-ray CT image while reducing the exposure of the object. Therefore, for example, even when performing X-ray CT imaging of children, who are small-sized object, it is possible to obtain X-ray CT images with good image quality and prevent unnecessary exposure to the object.

In general, when performing tube current modulation imaging, the X-ray CT apparatus modulates the tube current by controlling the filament current applied to the cathode filament of the X-ray tube. However, there is a time lag between the time when the filament current is applied and the time when the filament is heated to emit the desired amount of thermal electrons. Therefore, when modulating the tube current rapidly, the tracking of the filament temperature may be delayed. Therefore, in the method of modulating the tube current by controlling the filament current, the magnitude of the time variation (rate of change) of the tube current is limited according to the responsiveness of the filament temperature change. When this kind of limitation is imposed, it may become difficult to perform imaging, for example, the imaging of the chest of the human body, that requires a large range of tube current change, i.e., rapid tube current modulation.

As a technique to speed up the tube current modulation, there is a technique to control the tube current by applying a voltage to the grid electrodes in the cathode of the X-ray tube. However, in the case of controlling the tube current modulation using only the grid voltage, it is necessary to always apply a high filament current, which significantly impairs the filament life. In addition, to modulate the tube current, a high voltage waveform of several hundred to several thousand volts must be applied to the grid, and thus, a large power supply device such as a high-speed and high-voltage amplifier is required to control the grid voltage precisely and quickly. In the case of the X-ray CT apparatus, which has a limited mounting volume, it is difficult to mount a large power supply, and it is difficult to realize precise and fast feedback control of the grid voltage.

DETAILED DESCRIPTION

Hereinbelow, a description will be given of an X-ray CT apparatus according to embodiments of the present invention with reference to the drawings.

In general, according to one embodiment, an X-ray CT apparatus includes processing circuitry. The processing circuitry is configured to acquire set tube current waveform, and specify, based on the set tube current waveform, a period of a first tube current and a period of a second tube current lower than the first tube current. The processing circuitry is further configured to determine a waveform of a grid voltage such that a first grid voltage is applied during a period corresponding to the period of the first tube current and a second grid voltage, which is higher than the first grid voltage, is applied during a period corresponding to the period of the second tube current.

Figure 1:
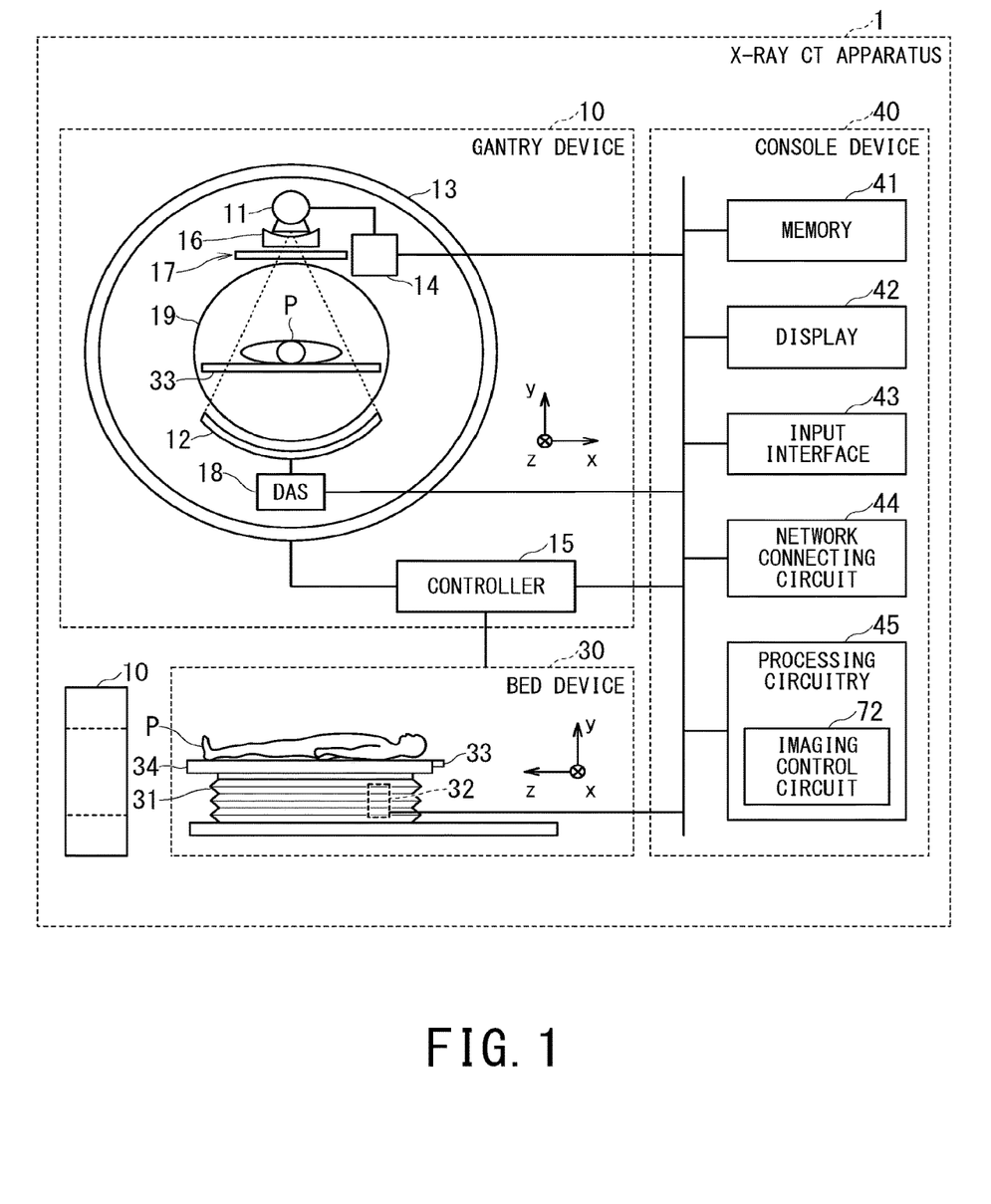
FIG. 1 is a block diagram showing an example configuration of an X-ray CT apparatus according to an embodiment.
Figure 2:
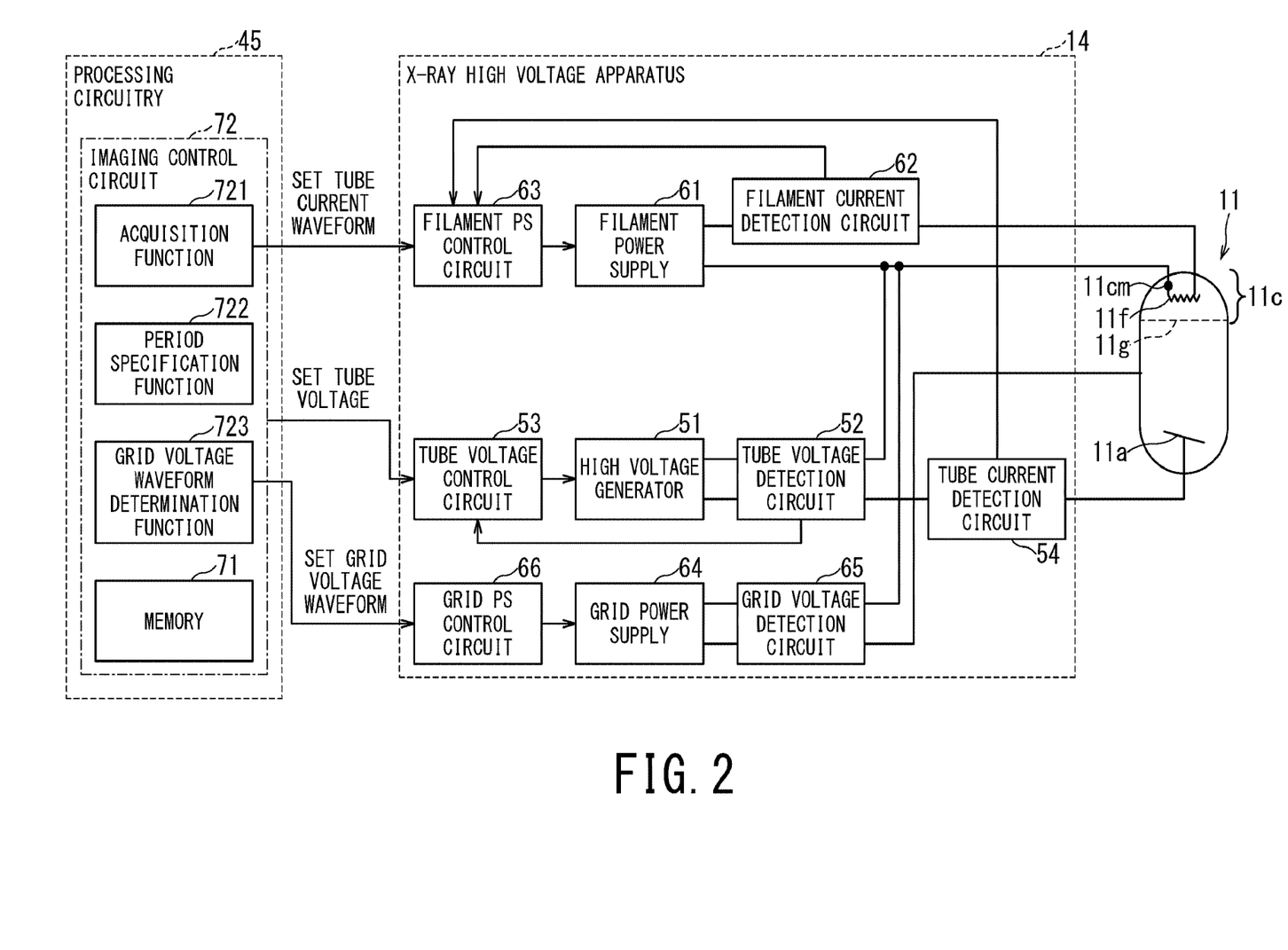
FIG. 2 is a block diagram showing an example configuration of an X-ray high voltage apparatus and a processing circuitry according to an embodiment.

FIG. 1 is a block diagram showing an example configuration of the X-ray CT apparatus 1 according to an embodiment. FIG. 2 is a block diagram showing an example configuration of the X-ray high voltage apparatus 14 and a processing circuitry according to an embodiment. The X-ray CT apparatus 1 shown in FIG. 1 has a single gantry device 10, but two gantry devices 10 are depicted in FIG. 1 for convenience of explanation.

The X-ray CT apparatus 1 includes the gantry device 10, the bed device 30, and the console device 40. The X-ray high voltage apparatus 14 can also be applied to dental CT apparatuses.

As shown in FIG. 1, in the present embodiment, the rotational axis of the rotating frame 13 in the non-tilted state or the longitudinal direction of the tabletop 33 of the bed device 30 is defined as the z-axis direction, the direction orthogonal to the z-axis and parallel to the floor surface is defined as the x-axis direction, and an axial direction perpendicular to the floor surface is defined as the y-axis direction.

The X-ray CT apparatus 1 may be configured as any one of different types, such as a so-called third generation CT apparatus, i.e., an Rotate/Rotate type in which an X-ray tube and an X-ray detector integrally rotate about the object P, or as a so-called fourth generation CT apparatus, i.e., an Stationary/Rotate type or an Nutate/Rotate type in which multiple detecting elements are circularly arrayed and only the X-ray tube rotates about the object P. In the following, an example of adopting the third generation Rotate/Rotate type as the X-ray CT apparatus 1 according to the present embodiment is explained.

The gantry device 10 includes the X-ray tube 11, the X-ray detector 12, the rotating frame 13 having the opening portion 19 in which an imaging region resides, the X-ray high voltage apparatus 14, the controller 15, the wedge 16, the collimator 17, and the DAS (Data Acquisition System) 18.

The X-ray tube 11 has a vacuum tube that houses the cathode 11*c* and the anode 11*a*. The cathode 11*c* has a filament 11*f* and a grid electrode 11*g*. The thermal electrons emitted from the filament 11*f* are accelerated by a high voltage applied between the common terminal 11*cm* at one end of the filament 11*f* and the anode 11*a* by the X-ray high voltage apparatus 14, and collide with the anode 11*a* to generate X-rays.

As shown in FIG. 2, the common terminal 11*cm*, which is connected to one end of the filament 11*f*, and the anode 11*a* are connected to the high voltage generator 51. The filament power supply 61 is connected to the filament 11*f*, and the grid power supply 64 is connected between the common terminal 11*cm* and the grid electrode 11*g*. A grid voltage with respect to the cathode potential is applied to the grid electrode 11*g* by the grid power supply 64 according to the grid voltage waveform determined by the X-ray high voltage apparatus 14 based on the set tube current waveform. By applying the grid voltage to the grid electrode 11*g*, the amount of thermal electrons flying from the cathode 11*c* to the anode 11*a* is suppressed, and the tube current value is reduced. The grid voltage waveform will be described later using FIGS. 2-6.

The X-ray tube 11 of the present embodiment is applicable to both single-tube X-ray CT apparatuses and so-called multi-tube X-ray CT apparatuses in which multiple pairs of X-ray tubes and detectors are mounted on a rotating ring.

The X-ray detector 12 detects X-rays that is irradiated from the X-ray tube 11 and passes through the object P, and outputs an electric signal corresponding to the detected amount of X-rays to the DAS 18. The X-ray detector 12 has, for example, a plurality of X-ray detection element arrays in which a plurality of X-ray detection elements are arrayed in the channel direction along one circular arc around the focus of the X-ray tube 11. For example, the X-ray detector 12 has a structure in which the plurality of X-ray detection element arrays in the channel direction is arrayed in a slice direction (column direction, row direction).

The X-ray detector 12 is, for example, an indirect conversion type detector having a grid, a scintillator array, and an optical sensor array. The scintillator array has a plurality of scintillators, and each scintillator has a scintillator crystal that outputs light with an amount of photons corresponding to the amount of incident X-rays. The grid is disposed on the X-ray incident side of the scintillator array and has an X-ray shielding plate having a function of absorbing scattered X-rays. The grid may also be referred to as a collimator (1D collimator or 2D collimator). The optical sensor array has a function of converting the light from the scintillator into an electric signal corresponding to the amount of the light from the scintillator, and has, for example, an optical sensor such as a photomultiplier tube (PMT).

The X-ray detector 12 may be a direct conversion type detector having a semiconductor element for converting incident X-rays into electric signals.

The rotating frame 13 is an annular frame that supports the X-ray tube 11 and the X-ray detector 12 so as to face each other and rotates the X-ray tube 11 and the X-ray detector 12 by the controller 15 described below. In addition to the X-ray tube 11 and the X-ray detector 12, the rotating frame 13 further includes and supports the X-ray high voltage apparatus 14 and the DAS 18.

The detection data generated by the DAS 18 is transmitted from a transmitter having a light emitting diode (LED) provided in the rotating frame 13 by optical communication to a receiver having a photo diode provided in a non-rotating portion of the gantry device 10, e.g., a fixed frame (not shown), and is then transferred to the console device 40. The method of transmitting the detection data from the rotating frame 13 to the non-rotating part of the gantry device 10 is not limited to the above-mentioned optical communication, and any method may be adopted as long as it is non-contact type data transmission.

The X-ray high-voltage apparatus 14 may be installed on the rotating frame 13 or on the fixed frame side of the gantry device 10. Details of the configuration and operation of the X-ray high-voltage apparatus 14 will be described later using FIGS. 2-6.

The controller 15 has a processor, a memory, and a driving mechanism such as a motor and an actuator. The controller 15 receives an input signal from the input interface 43 attached to the console device 40 or the gantry device 10, and controls the gantry device 10 and the bed device 30. For example, the controller 15 performs rotation control of the rotating frame 13 in response to the input signal, tilt control of the gantry device 10, and driving control of the bed device 30 and the tabletop 33. The tilt control of the gantry device 10 is made by the controller rotating the rotating frame 13 around an axis parallel to the X axis direction on the basis of the tilt angle information input by the input interface attached to the gantry device 10. The controller 15 may be provided in the gantry device 10 or may be provided in the console device 40.

The wedge 16 is a filter for adjusting the amount of X-rays irradiated from the X-ray tube 11. Specifically, the wedge 16 transmits and attenuates the X-rays irradiated from the X-ray tube 11 such that the X-rays applied to the object P from the X-ray tube 11 have a predetermined distribution. For example, the wedge 16 (wedge filter, bow-tie filter) is a filter in which aluminum is processed to have a predetermined target angle or a predetermined thickness.

The collimator 17 is a lead plate or the like for narrowing the irradiation range of the X-rays transmitted through the wedge 16, and forms a slit by combining a plurality of lead plates or the like. The collimator 17 may be called an X-ray movable diaphragm.

The DAS 18 includes an amplifier that performs amplification processing on electric signals output from the respective X-ray detecting elements of the X-ray detector 12 and an A/D converter that converts the electric signals into digital signals, and generates detection data. The detection data generated by the DAS 18 is transferred to the console device 40.

The bed device 30 is a device for placing and moving the object P to be scanned, and includes a base 31, a bed driving device 32, the tabletop 33, and a support frame 34.

The base 31 is a casing that supports the support frame 34 movably in the vertical direction (y direction). The bed driving device 32 is a motor or an actuator that moves the tabletop 33 on which the object P is placed in the longitudinal direction (z direction) of the tabletop 33. A tabletop 33 provided on the upper surface of the support frame 34 is a plate on which the object P is placed.

In addition to the tabletop 33, the bed driving device 32 may move the support frame 34 in the long axis direction (z direction) of the tabletop 33. Further, the bed driving device 32 may be moved together with the base 31 of the bed device 30. In the case where the present invention can be applied to a standing CT (an X-ray CT apparatus adapted to a standing object), the patient movement mechanism may be moved instead of the tabletop 33.

The console device 40 has the memory 41, the display 42, the input interface 43, the network connecting circuit 44, and the processing circuitry 45. Although the console device 40 is described as a separate entity from the gantry device 10, some or all of the components of the console device 40 may be included in the gantry device 10. The console device 40 is described below as a single console that performs all functions, but these functions may be performed by multiple consoles.

The memory 41 includes a processor-readable recording medium such as a semiconductor memory element, e.g., a RAM (Random Access Memory) or a flash memory, a hard disk, an optical disk, and the like. The memory 41 stores projection data, reconstructed image data, and volume data of object P acquired in advance.

The display 42 displays various kinds of information. For example, the display 42 outputs a medical image (CT image) generated by the processing circuitry 45, a GUI (Graphical User Interface) for receiving various operations from the user, and the like. For example, the display 42 is a liquid crystal display, CRT (Cathode Ray Tube) display, OLED (Organic Light Emitting Diode) display, or the like. The display 42 may be provided on the gantry device 10. The display 42 may be a desktop type, or it may consist of a tablet device that can communicate wirelessly with the main body of the console device 40.

The input interface 43 accepts various input operations from the user, converts the accepted input operations into electric signals, and outputs them to the processing circuitry 45. For example, the input interface 43 receives from the user the collection conditions for collecting projection data, the reconstruction conditions for reconstructing a CT image, the image processing conditions for generating a post-processing image from a CT image, and the like. The input circuit 21 may be realized by general input devices such as a mouse, a keyboard, a trackball, a switch, a button, a joystick, a touch pad that performs an input operation by touching an operation surface, a touchscreen that integrates the display screen with the touchpad, a contactless input circuit using an optical sensor, a voice input circuit, and the like. The input interface 43 may be provided on the gantry device 10. The input interface 43 may consist of a tablet terminal or other device that can wirelessly communicate with the console device 40.

The network connecting circuit 44 implements various information communication protocols according to the network. The network connecting circuit 44 connects the X-ray CT apparatus 1 and other devices such as an image server in accordance with these various protocols. For this connection, electrical connection via an electronic network or the like can be applied. The network refers to a general information communication network using telecommunications technology and includes not only a wireless/wired LAN hospital backbone local area network (LAN) and the Internet network, but also a telephone communication network, an optical fiber communication network, a cable communication network, a satellite communication network, and other networks.

The processing circuitry 45 is a processor configured to control the entire operation of the X-ray CT apparatus 1 by reading out and executing the program stored in the memory 41. The processing circuitry 45 controls the X-ray high voltage apparatus 14, the controller 15, and the DAS 18 according to the imaging conditions determined by the scan plan and the like.

The processing circuitry 45 according to the present embodiment is further described as including the imaging control circuit 72. The imaging control circuit 72 will be described later.

(Configuration of the X-Ray High Voltage Apparatus)

Next, the configuration of the X-ray high voltage apparatus 14 will be explained.

As shown in FIG. 2, the X-ray high voltage apparatus 14 includes the high voltage generator 51, the tube voltage detection circuit 52, the tube voltage control circuit 53, tube current detection circuit 54, the filament power supply 61, the filament current detection circuit 62, the filament power supply control circuit 63, the grid power supply 64, the grid voltage detection circuit 65, and the grid power supply control circuit 66.

The processing circuitry 45 of the console device 40 shown in FIG. 1 has the imaging control circuit 72, and the X-ray high voltage apparatus 14 controls X-ray output according to the instructions of the imaging control circuit 72 described below.

The high voltage generator 51 has electrical circuits such as a transformer and a rectifier, and has the function of generating high voltage to be applied to the X-ray tube 11, and the output voltage thereof is controlled by the tube voltage control circuit 53. The high voltage generator 51 may be a transformer system or an inverter system. The tube voltage detection circuit 52 detects the tube voltage of the X-ray tube 11 and outputs a signal according to the detected tube voltage value to the tube voltage control circuit 53. The tube voltage control circuit 53 controls the output voltage of the high voltage generator 51 such that the tube voltage detected by the tube voltage detection circuit 52 approaches the set tube voltage value set by the imaging control circuit 72.

The tube current detection circuit 54 detects the tube current value applied to the X-ray tube 11, and outputs a signal according to the detected tube current value to the filament power supply control circuit 63.

The filament power supply 61 is a current source that generates a filament current applied to the filament 11$f$ to heat the filament 11$f$ of the cathode 11$c$ of the X-ray tube 11, and the output current thereof is controlled by the filament power supply control circuit 63.

The filament current detection circuit 62 detects the filament current and outputs a signal according to the detected filament current value to the filament power supply control circuit 63.

The filament power supply control circuit 63 feedback controls the output current of the filament power supply 61 such that the tube current value detected by the tube current detection circuit 54 approaches the tube current value of the set tube current waveform set by the imaging control circuit 72.

As shown in FIG. 2, an example of a case where the filament 11$f$ is used as the filament member that emits thermal electrons is described in the present embodiment, but a flat emitter may also be used as the filament member.

The grid power supply 64 is a power supply that applies a grid voltage between the common terminal 11cm of the cathode 11c of the X-ray tube 11 and the grid electrode 11g, and is controlled by the grid power supply control circuit 66. Typically, the grid voltage is applied by the grid power supply 64. The grid power supply 64 may be realized by a step-down circuit that steps down the voltage generated by high voltage generator 51, or by a power supply independent of the high voltage generator 51.

The grid power supply control circuit 66 feedback controls the output voltage of the grid power supply 64 such that the grid voltage value detected by the grid voltage detection circuit 65 approaches the grid voltage value of the set grid voltage waveform set by the imaging control circuit 72.

The imaging control circuit 72 includes the acquisition function 721, the period specification function 722, the grid voltage waveform determination function 723, and the memory 71.

The imaging control circuit 72 calculates and sets the setting values for the filament power supply control circuit 63, the tube voltage control circuit 53, and the grid power supply control circuit 66 based on the information set by the processing circuitry 45 of the console device 40 in FIG. 1. The imaging control circuit 72 is a processor that reads out and executes the tube current modulation program stored in memory 71 to achieve high modulation of the tube current by slowing down the rate of change of the filament temperature in the tube current modulation control to a level that can be tracked (followed).

The processor of the imaging control circuit 72 realizes the acquisition function 721, the period specification function 722, and the grid voltage waveform determination function 723, as shown in FIG. 2. Each of these functions is stored in memory 71 in the form of a program.

The acquisition function 721 acquires the set tube current waveform and gives it to the filament power supply control circuit 63. It is preferable that the set tube current waveform is set according to at least one of the shape and size of the object. For example, when the inspection order information includes the set tube current waveform, the acquisition function 721 acquires the set tube current waveform from the inspection order information. The set tube current waveform may also be entered by the user via the input interface 43. When, for example, the inspection order information includes information suggesting the shape and size of the object, such as age, weight, height, and the like, the acquisition function 721 may acquire the set tube current waveform by creating the waveform based on this information.

The period specification function 722 specifies, based on the set tube current waveform, the period of the first tube current (hereinafter referred to as the first tube current period) T1, which will be described later using FIG. 5, and the period of the second tube current (hereinafter referred to as the second tube current period) T2, to which a tube current value lower than the tube current belonging to the first tube current period T1 belongs.

The grid voltage waveform determination function 723 determines the grid voltage waveform such that the first grid voltage is applied in the first grid period Tg1 corresponding to the first tube current period T1, which will be described later using FIG. 5, and the second grid voltage, which is higher than the first grid voltage, is applied in the second grid period Tg2 corresponding to the second tube current period T2. The grid voltage waveform determination function 723 outputs the grid voltage to the grid power supply 64 via the grid power supply control circuit 66 in accordance with the determined grid voltage waveform.

Although the imaging control circuit 72 is described as being provided in the processing circuitry 45 included in the console device 40, the imaging control circuit 72 may be provided in the X-ray high voltage apparatus 14, or may be provided independently between the processing circuitry 45 of the console device 40 and the X-ray high voltage apparatus 14.

The memory 71 has a configuration including, for example, semiconductor memory devices such as RAM (Random Access Memory) and flash memory, hard disks, optical disks, and other recording media readable by the processor, and stores programs and various data. The memory 71 may, for example, store in advance a threshold value for identifying periods T1, T2, and the like in the set tube current waveform, which will be described later using FIG. 5. Memory 71 may also store in advance a table in which tube voltage, tube current, and focal spot size are associated. Some or all of the programs and data stored in memory 71 may be downloaded by communication via an electronic network, or may be stored on a portable storage medium such as an optical disk. Some or all of the programs and data stored in memory 71 may be downloaded by communication through an electronic network, or may be given to memory via a portable storage medium such as an optical disk.

(Tube Current Modulation Control by Filament Current Only)

Figure 3:
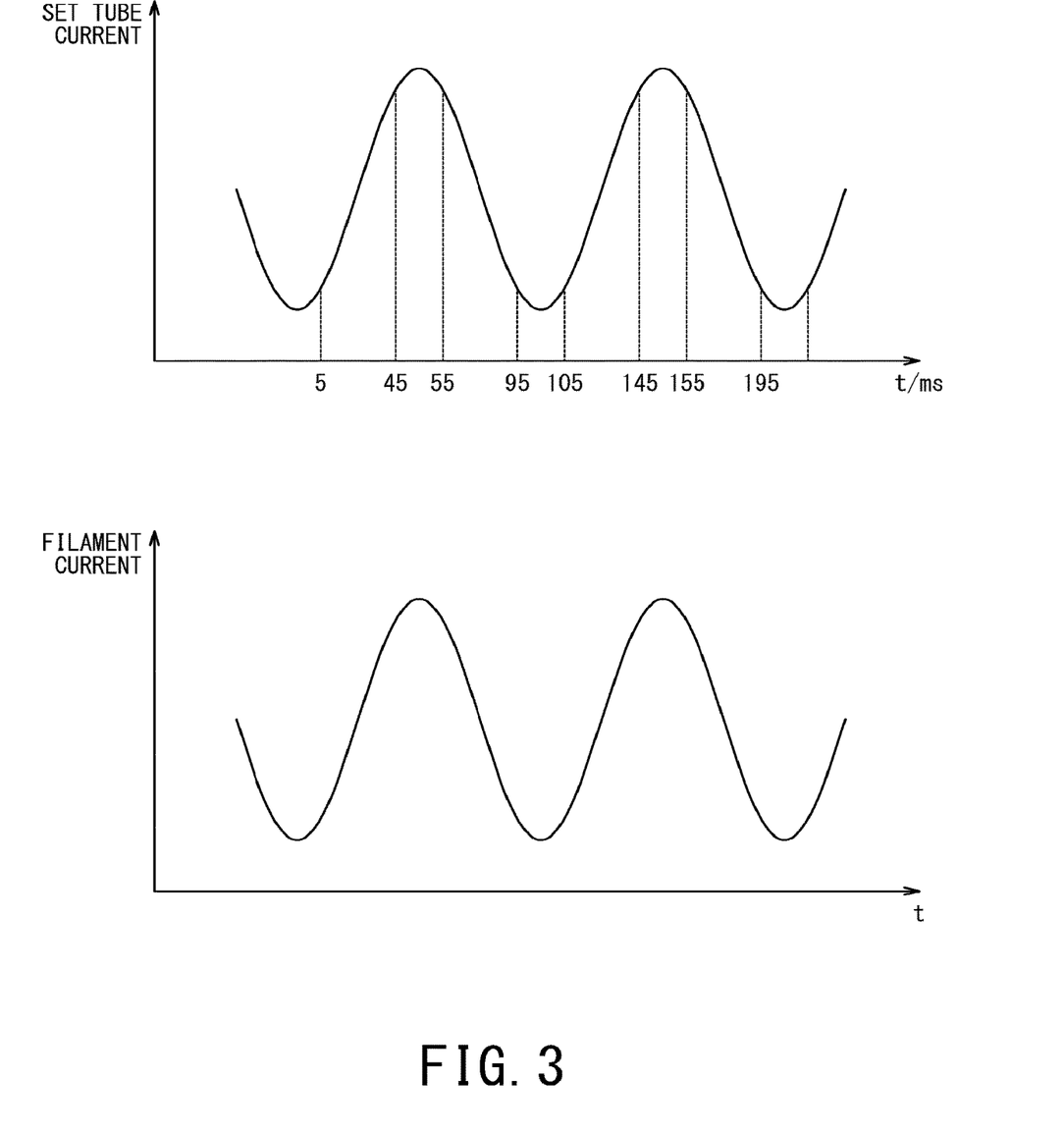
FIG. 3 is an explanatory diagram showing an example of the relationship between the set tube current waveform and the filament current control waveform when tube current modulation control is performed using only the filament current.
Figure 4:
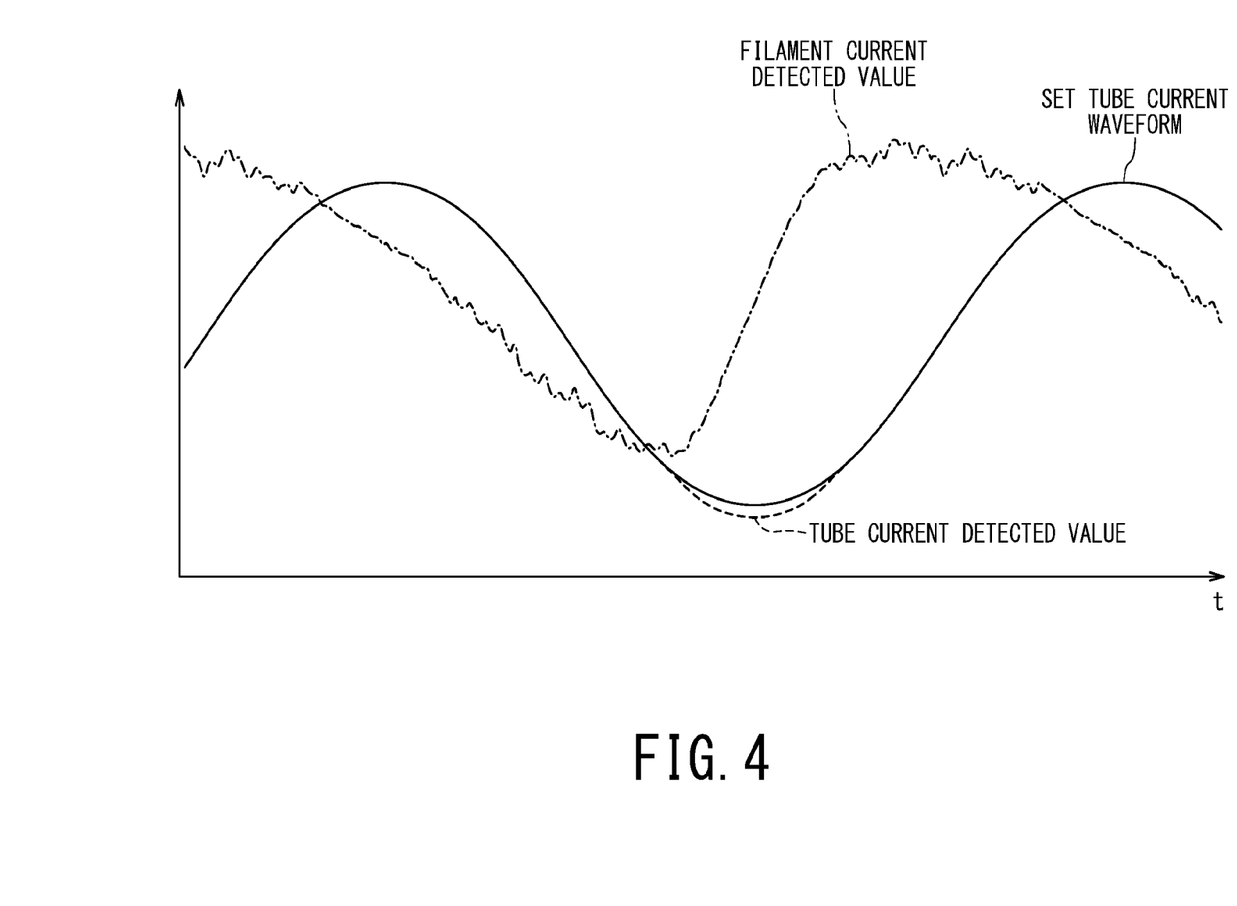
FIG. 4 is a diagram for explaining a case where tube current modulation control is performed using only the filament current and the tube current modulation is operated near the tracking limit of the filament temperature.

FIG. 3 is an explanatory diagram showing an example of the relationship between the set tube current waveform and the filament current control waveform when tube current modulation control is performed using only the filament current. FIG. 4 is a diagram for explaining a case where tube current modulation control is performed using only the filament current and the tube current modulation is operated near the tracking limit of the filament temperature. In the following explanation, an example of the case where the set tube current waveform has a sinusoidal shape is shown, but the shape of the set tube current waveform can be any shape with periodicity and is not limited to a sinusoidal wave.

As shown in FIG. 3, in the case of tube current modulation control using only filament current, the filament current waveform is a sinusoidal wave of the same cycle when the set tube current waveform is a sinusoidal wave. In the following explanation, the filament current waveform corresponding to the set tube current waveform in the case of tube current modulation control using only filament current, is referred to as "simple filament current waveform".

However, as described above, there is a time delay between the application of the filament current and the rise of the filament temperature to emit the desired amount of thermal electrons, and the response of the tube current is delayed when the tube current is modulated rapidly. Further, even when the filament current is decreased to cool the filament rapidly, the response of the tube current is delayed because the cooling of the filament temperature cannot follow the change of the filament current. In particular, when the tube current change rate (change speed) is near the limit of the filament temperature tracking, as shown in FIG. 4, even when the tube current is detected to have fallen below the set value and the filament current is reheated, it takes time for the tube current to respond, and an undershoot may occur where the detected value of the tube current is smaller than the tube current value of the set tube current waveform. Thus, when tube current modulation is performed only by the thermal change of the filament, the tube current modulation waveform collapses from the set tube current waveform under the condition that the filament current changes rapidly because of the slow thermal response of the filament.

Therefore, the X-ray high voltage apparatus 14 according to the present embodiment uses the phenomenon that the tube current becomes smaller when the grid voltage is applied, and modulates the tube current by combining the grid voltage change and the filament current change. An example is described below.

(Tube Current Modulation Control According to the Present Embodiment)

Figure 5:
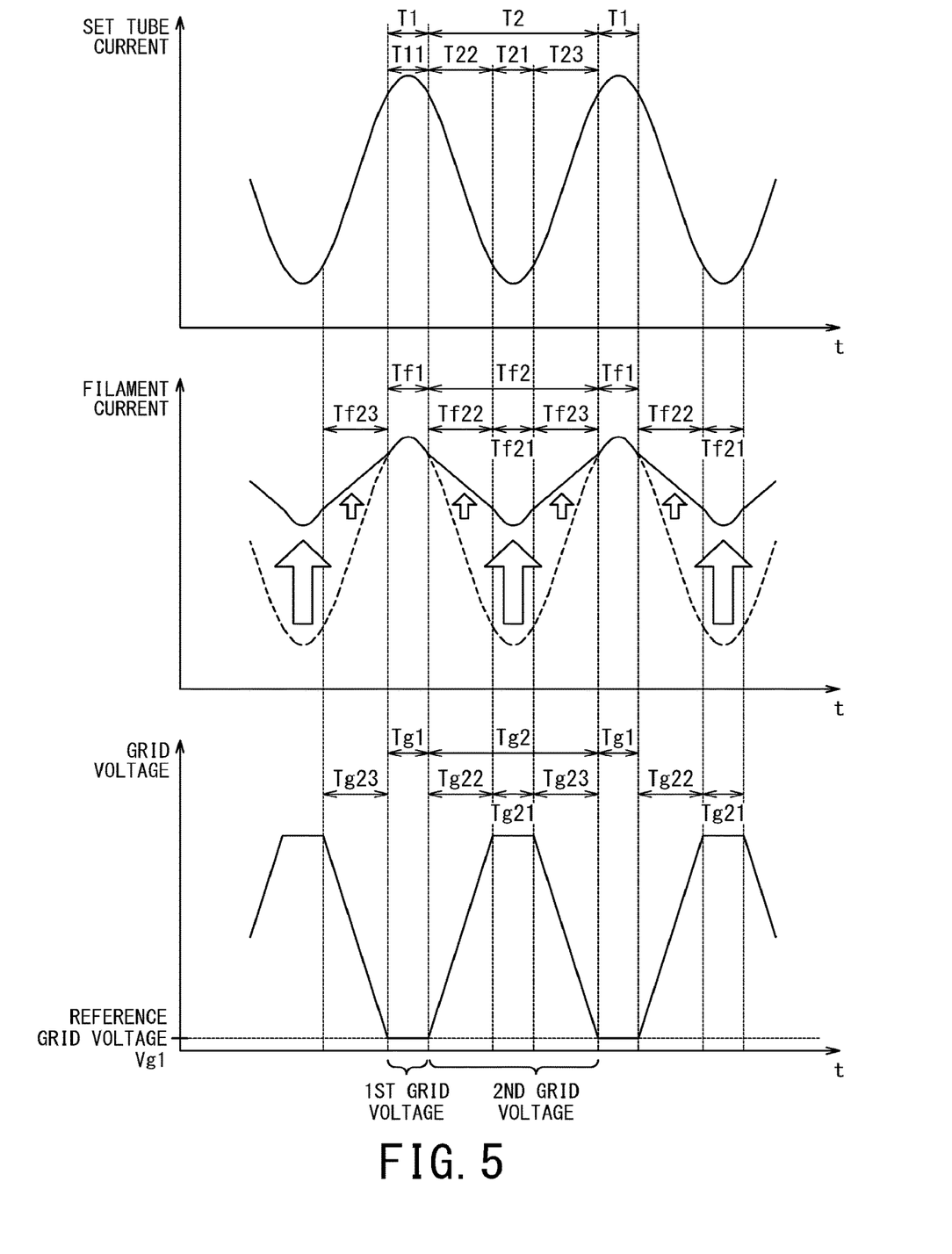
FIG. 5 is a diagram for explaining tube current modulation control according to the present embodiment in which a grid voltage change and a filament current change are combined.

FIG. 5 is a diagram for explaining tube current modulation control according to the present embodiment in which a grid voltage change and a filament current change are combined. As shown in FIG. 4, the peak of the set tube current waveform has a time difference from the peak of the filament current and the peak of the grid voltage resulted from the thermal response of the filament, but in FIG. 5, each waveform is shifted so that the peaks coincide for convenience.

The waveform shown by the dashed line in the middle of FIG. 5 is the simple filament current waveform, which is the filament current waveform when only the filament current is modulated with a constant grid voltage and controlled to be the set tube current as shown in the upper part of FIG. 5.

In the following, each period of the filament current waveform corresponding to each period Ti of the set tube current waveform (where i represents a number) is described as Tfi, and each period of the grid voltage waveform as Tgi.

The period specification function 722 calculate the magnitude of the change speed (time change) of the tube current from the set tube current waveform obtained by the acquisition function 721, and compares the calculated magnitude with the tube current response characteristics of the X-ray tube. Based on the comparison result, when the tube current change rate is larger than the tube current response characteristic of the X-ray tube, it is regarded as a period in which correction control by the grid voltage is required in addition to the tube current control by the filament current, and the first tube current period T1 and the second tube current period T2, to which the tube current value lower than the tube current belonging to the first tube current period T1 belongs, are specified. The necessity of the correction control by the grid voltage may be determined by the threshold ratio of the maximum amplitude of the set tube current waveform (e.g., 60% or more of the maximum current value).

For example, assuming the periods in which the tube current change rate in time section of a single slice is smaller than the tube current response characteristics of the X-ray tube are T11 and T21, and the periods in which the tube current change rate is greater than the tube current response characteristics of the X-ray tube are T22 and T23, then the first tube current period T1 is specified as the period T11 that includes the highest current value in the set tube current waveform. The first tube current period T1 may be specified as a period that includes the highest current value in the set tube current waveform and is smaller than or equal to a threshold ratio (e.g. 10%) of the maximum amplitude of the set tube current waveform.

The second tube current period T2 is specified as a period other than the first tube current period T1.

The grid voltage waveform determination function 723 determines the grid voltage waveform such that the grid voltage (the second grid voltage) Vg2 of the second grid period Tg2 corresponding to the second tube current period T2 is higher than the grid voltage (the first grid voltage) Vg1 of the first grid period Tg1 corresponding to the first tube current period T1. The grid voltage Vg1 applied to the first grid period Tg1 corresponding to the first tube current period T1 is hereinafter referred to as the reference grid voltage Vg1. The information on the reference grid voltage Vg1 may be included in the X-ray setting conditions acquired by the acquisition function 721.

When the grid voltage is applied, the tube current is decreased without decreasing the filament current. Therefore, the higher the grid voltage is applied, the higher the filament current is required than the simple filament current waveform corresponding to the set tube current waveform. Therefore, the higher the grid voltage is applied, the filament current waveform becomes a shape that the bottom of the simple filament current waveform is pushed upward as illustrated by the dashed line in the middle of FIG. 5.

Therefore, by determining the grid voltage waveform so that the grid voltage in the second grid period Tg2 is higher than the grid voltage Vg1 in the first grid period Tg1, the difference between the filament current in the first filament period Tf1 and the filament current in the second filament period Tf2 becomes relatively smaller. In this case, the change range of the filament temperature becomes smaller, and thus, the change rate of the filament temperature naturally becomes smaller. Therefore, by using the grid voltage, the change rate of the filament temperature in the tube current modulation control can be slowed down. Accordingly, by using the grid voltage, the tube current can be modulated with a larger change rate than the limit of the tube current change rate in the case of tube current modulation using only the filament current without using the grid voltage.

The period specification function 722 may further classify and specify the second tube current period T2 into a plurality of section elements. In this case, as described above, the period specification function 722 may classify and specify the period in which the tube current change rate during one slice section is smaller than the tube current response characteristics of the X-ray tube into the first tube current period element T21, and classify and specify the period in which the tube current change rate is larger than the tube current response characteristics of the X-ray tube into the second tube current period element T22 and the third tube current period element T23. (see the upper part of FIG. 5). The first tube current period element T21 may be specified as the period including the lowest current value in the set tube current waveform and the period in which the magnitude (absolute value) of the time change (change speed) of the tube current is smaller than the threshold value or smaller than the threshold ratio (e.g., 10%) of the maximum amplitude of the set tube current waveform. The second tube current period element T22 may be set as a downward period from the end of the first tube current period T1 to the beginning of the first tube current period element T21, and the third tube current period element T23 may be set as an upward period from the end of the first tube current period element T21 to the beginning of the first tube current period T1.

In the case where the set tube current waveform is a sinusoidal wave, the aforementioned threshold value and threshold ratio for specifying the first tube current period T1 and the first tube current period element T21 may be set to specify the first tube current period T1 and the first tube current period element T21 as the periods in the sinusoidal wave in which the error in linear approximation deviates by a predetermined ratio or more.

The grid voltage waveform determination function 723 may make the second grid voltage in the second grid period Tg2 different for each period element. The first filament period element Tf21 is the period when the filament current is at its minimum value. Therefore, the grid voltage waveform determination function 723 may determine the second grid voltage for each period element such that the grid voltage in the first grid period element Tg21 is higher than the grid voltage in the second and third grid period elements Tg22 and Tg23.

By applying the highest grid voltage at the first grid period element Tg21, which corresponds to the first tube current period element T21 where the smallest tube current value is required, the minimum filament current value is lifted significantly by the tube current suppression effect of the grid voltage. As a result, the speed of change of the filament temperature becomes smaller, which greatly improves the temperature tracking and the accuracy of the tube current modulation (see the middle of FIG. 5).

The x-ray high voltage apparatus 14 may perform static grid voltage control with the grid voltage at a constant value and obtain the set tube current value by feedback control of the filament current in periods when the change rate (slope) of the set tube current is small, such as the first tube current period T1 (the change rate of the tube current is equal to the period T11, which is smaller than the tube current response characteristic of the X-ray tube in the example shown in FIG. 5) and the first tube current period element T21, or in the period when the change rate is small but precise tube current control is required.

Meanwhile, the x-ray high voltage apparatus 14 may change the grid voltage almost linearly such that the change width of the filament current becomes small in the periods such as the second and third tube current period elements T22 and T23, where the change speed of the set tube current is larger than the filament current response speed and the set tube current changes linearly and the change speed (slope) can be regarded as almost constant.

The lower part of FIG. 5 shows an example of a case where the grid voltage waveform is determined to be a trapezoidal shape, the diagonal of which is formed with the second tube current period element T22 and the third tube current period element T23. In this case, as shown in the middle part of FIG. 5, dynamic grid voltage control is performed in the periods corresponding to the second and third tube current period elements T22 and T23, where the time change of the tube current is large (the slope of the tube current waveform is large), and feedback control of the filament current is used for fine adjustment of the error with the set tube current as a supplement. In the first tube current period T1 and the first tube current period element T21, where the time change of the tube current is small (near the extreme value of the tube current waveform), the filament current feedback control is used to follow the set tube current value, while the static grid voltage control is used without changing the grid voltage because it is difficult to control the grid voltage at high speed.

Thus, by combining the grid voltage change and filament current change according to the magnitude of the tube current time change, the filament temperature change rate can be significantly reduced compared to the tube current modulation control using only the filament current. Therefore, the accuracy of the tube current modulation can be greatly improved, and the amount of X-ray irradiation can be optimized to obtain X-ray CT images of suitable quality while reducing the amount of exposure. Hence, even imaging that requires a large tube current change rate, for example, in the chest of the human body, can be easily performed.

In addition, compared to the tube current modulation control using only the grid voltage, the tube current modulation control can be performed accurately with a simple configuration because feedback control of the grid voltage is not necessary. Since the X-ray high voltage apparatus 14 according to the present embodiment combines the grid voltage change and filament current change according to the magnitude of the time variation of the tube current, there is no need to keep applying a high filament current all the time and there is no risk of damaging the life of the filament.

Within the permissible range that can be followed without changing the configuration of the grid power supply 64, the diagonals of the trapezoidal shape of the grid voltage waveform may be a curve corresponding to the curve of the corresponding period of the set tube current waveform instead of a straight line. The upper and lower bottoms of the trapezoidal shape may be similarly curved according to the curve of the corresponding period of the set tube current waveform within the allowable range of the grid power supply 64.

Figure 6:
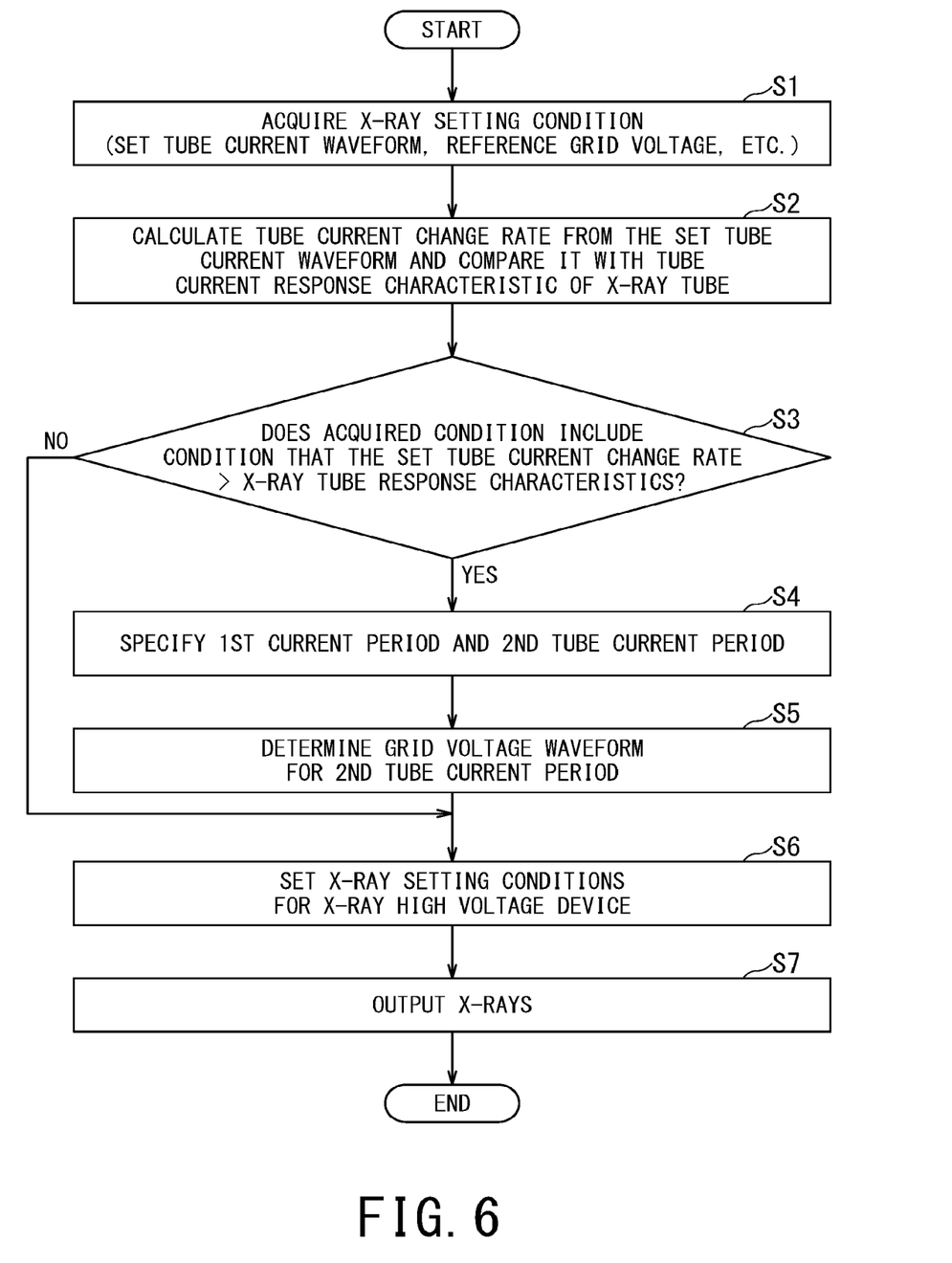
FIG. 6 is a flowchart showing an example of a procedure for slowing the rate of change in filament temperature in tube current modulation control by the X-ray CT apparatus shown in FIG. 1.

FIG. 6 is a flowchart showing an example of a procedure for slowing the rate of change in filament temperature in tube current modulation control. In FIG. 6, a reference character with "S" followed by a number denotes each step of the flowchart.

First, in step S1, the acquisition function 721 acquires X-ray setting conditions based on the inspection order information and the like. The X-ray setting conditions include the set tube current waveform based on at least one of the shape and size of the object. The X-ray setting conditions may also include information on the reference grid voltage Vg1.

Next, in step S2, the period specification function 722 calculates the tube current change rate from the set tube current waveform and compares the calculated rate with the tube current response characteristics of the X-ray tube. When the set tube current change rate is smaller than or equal to the X-ray tube response characteristic (NO in step S3), proceed to step S6. In the meantime, when the set tube current change rate is greater than the X-ray tube response characteristic (YES in step S3), proceed to step S4.

To determine whether to proceed to step S4, it is possible to proceed to S4 when the set tube current change width (tube current waveform amplitude in FIG. 5) is greater than a certain threshold (e.g., 60% of the highest current value in the section). The threshold value may be different for the highest tube current value, focal size setting, and tube current.

Next, in step S4, the first tube current period T1 and the second tube current period T2 is specified in a certain time section to which the tube current value lower than the tube current belonging to the first tube current period T1 belongs, for example, during one slice (see the upper part of FIG. 5).

Next, in step S5, the grid voltage waveform determination function 723 determines the grid voltage waveform such that the first grid voltage Vg1 is applied to the first grid period Tg1 corresponding to the first tube current period T1 and the second grid voltage Vg2, which is higher than the first grid voltage Vg1, is applied to the second grid period Tg2 corresponding to the second tube current period T2 (see the lower part of FIG. 5). When the imaging conditions includes imaging of multiple slices and the set tube current waveform is different for each slice, steps S4 and S5 are performed for each slice or for each certain time section to determine the grid voltage waveform.

Next, in step S6, the grid voltage waveform determined by the grid voltage waveform determination function 723 and the X-ray setting conditions such as the set tube current waveform acquired in step S1 are set up in the X-ray high voltage apparatus 14.

Then, in step S7, the X-ray high voltage apparatus 14 controls the X-ray output based on the conditions set in step S6.

The change speed of the filament temperature in the tube current modulation control can be made slow by modulating the tube current by combining the grid voltage change and the filament current change based on the above procedure.

According to at least one of the above-described embodiments, the change rate of the filament temperature in the tube current modulation control can be slowed down.

The term "processor" used in the explanation in the above-described embodiments, for instance, refers to circuitry such as dedicated or general purpose CPUs (Central Processing Units), dedicated or general-purpose GPUs (Graphics Processing Units), or ASICs (Application Specific Integrated Circuits), programmable logic devices including SPLDs (Simple Programmable Logic Devices), CPLDs (Complex Programmable Logic Devices), and FPGAs (Field Programmable Gate Arrays), and the like. The processor implements various types of functions by reading out and executing programs stored in the memory circuitry.

In addition, instead of storing programs in the memory circuitry, the programs may be directly incorporated into the circuitry of the processor. In this case, the processor implements each function by reading out and executing each program incorporated in its own circuitry. Moreover, although in the above-described embodiments an example is shown in which the processing circuitry configured of a single processor implements every function, the processing circuitry may be configured by combining plural processors independent of each other so that each processor implements each function of the processing circuitry by executing the corresponding program. When a plurality of processors are provided for the processing circuitry, the memory medium for storing programs may be individually provided for each processor, or one memory circuitry may collectively store programs corresponding to all the functions of the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:
   processing circuitry configured to:
   acquire a set tube current waveform;
   specify, based on the set tube current waveform, a period of a first tube current and a period of a second tube current, which is lower than the first tube current; and
   determine a waveform of a grid voltage such that a first grid voltage is applied during a period corresponding to the period of the first tube current and a second grid voltage, which is higher than the first grid voltage, is applied during a period corresponding to the period of the second tube current.

2. The X-ray CT apparatus according to claim 1, further comprising:
   a tube current detection circuit configured to detect a tube current value applied to an X-ray tube;
   a filament power supply configured to generate a filament current for heating a filament of a cathode of the X-ray tube; and
   a filament control circuit configured to control the filament power supply such that the tube current value detected by the tube current detection circuit approaches a tube current value of the set tube current waveform.

3. The X-ray CT apparatus according to claim 1, wherein the processing circuitry is further configured to:
   specify, as a period element of the period of the second tube current, a period of time that includes a lowest current value in the set tube current waveform and in which a magnitude of a time change of a tube current value of the set tube current waveform is smaller than a threshold value or smaller than a threshold ratio of a maximum amplitude of the set tube current waveform; and
   determine a waveform of the second grid voltage such that a grid voltage applied during a period corresponding to the period element is higher than the grid voltage applied during the period corresponding to the period of the second tube current excluding the period element.

4. The X-ray CT apparatus according to claim 3, wherein the processing circuitry is further configured to determine the waveform of the grid voltage such that the grid voltage is a constant value during the period corresponding to the period of the first tube current and the period corresponding to the period element of the period of the second tube current, and the grid voltage is varied according to the second tube current during the period corresponding to the period of the second tube current excluding the period element.

5. The X-ray CT apparatus according to claim 4, wherein the processing circuitry is further configured to determine the waveform of the grid voltage such that the waveform of the grid voltage has a trapezoidal shape, a diagonal of which is formed with the period corresponding to the period of the second tube current excluding the period element.

6. The X-ray CT apparatus according to claim 3, wherein the processing circuitry is further configured to:
   specify, as the period of the first tube current, a period that includes a highest current value in the set tube current waveform and in which the magnitude of the time variation of the tube current is smaller than a threshold value or smaller than a threshold ratio of a maximum amplitude of the set tube current waveform; and
   determine a waveform of the grid voltage such that the first grid voltage applied during the period of the first tube current is a reference grid voltage.

7. An X-ray control method, comprising:
   acquiring a set tube current waveform;
   specifying, based on the set tube current waveform, a period of a first tube current and a period of a second tube current lower than the first tube current; and
   determining a waveform of a grid voltage such that a first grid voltage is applied during a period corresponding to the period of the first tube current and a second grid voltage, which is higher than the first grid voltage, is applied during a period corresponding to the period of the second tube current.

* * * * *